(12) United States Patent
Mikaelsson et al.

(10) Patent No.: US 6,599,724 B1
(45) Date of Patent: Jul. 29, 2003

(54) STABLE FACTOR VIII COMPOSITIONS

(75) Inventors: Marianne Mikaelsson, Bromma (SE); Helena Sandberg, Bromma (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/615,001

(22) Filed: Jul. 12, 2000

Related U.S. Application Data
(60) Provisional application No. 60/146,828, filed on Aug. 2, 1999.

(30) Foreign Application Priority Data

Jul. 13, 1999 (SE) .............................................. 9902685
May 11, 2000 (SE) .............................................. 0001743

(51) Int. Cl.⁷ ........................... C12N 9/94; C12P 21/06; C07K 1/00; C07K 14/00; C07K 16/00

(52) U.S. Cl. ....................... 435/183; 435/69.1; 424/529; 424/532; 424/94.67; 530/413; 530/416; 530/417

(58) Field of Search ................. 530/383, 413, 530/416, 417; 424/529, 532, 94.67; 435/183, 184, 69.1

(56) References Cited

U.S. PATENT DOCUMENTS

| 5,576,291 A | * | 11/1996 | Curtis et al. |
| 5,804,420 A | | 9/1998 | Chan et al. |
| 5,824,780 A | * | 10/1998 | Curtis et al. |

FOREIGN PATENT DOCUMENTS

| WO | WO8800210 | 1/1988 |
| WO | WO9407510 | 4/1994 |
| WO | WO9507713 | 3/1995 |
| WO | WO98 16629 | 4/1998 |

OTHER PUBLICATIONS

Gitschier et al, *Nature*, 312(22):326–330 (1984).
Wood et al, *Nature*, 312(22):330–337 (1984).
Vehar et al, *Nature*, 312(22)337–342 (1984).
Toole et al, *Nature*, 312(22):342–347 (1984).
Eaton et al, *The Journal of Biological Chemistry*, 262(7):3285–3290 (1987).
Andersson et al, *Proc. Natl. Acad. Sci. USA*, 83:2979–2983 (1986).
Roddie et al, *Blood Reviews*, 11:169–177 (1997).
Eis–Hubinger, A.M. et al, *Thrombosis and Haemostasis*, 76(1):120 (1996).
Berntorp, *Thrombosis and Haemostasis*, 78(1):256–260 (1997).
Mikaelsson et al, *Blood*, 62(5):1006–1015 (1983).
Fay, *Archives of Biochemistry and Biophysics*, 262(2):525–531 (1988).
Bihoreau et al, *European Journal of Biochemistry*, 222:41–48 (1994).
Pan Y. et al, *Nature Structural Biology*, 2:740–744 (1995).
Pemberton et al, *Blood*, 89(7):2413–2421 (1997).
Fatouros et al, *International Journal of Pharmaceutics*, 155:121–131 (1997).

* cited by examiner

Primary Examiner—Remy Yucel
Assistant Examiner—Konstantina Katcheves
(74) Attorney, Agent, or Firm—Fish & Richardson P.C.

(57) ABSTRACT

The present invention relates to a pharmaceutical composition comprising Factor VIII and the divalent metal ions $Zn^{2+}$ and $Cu^{2+}$, optionally in the presence of $Ca^{2+}$ ions and/or $Mn^{2+}$ ions, wherein said Factor VIII is stable without the addition of albumin. The invention also relates to a method for the production of recombinant Factor VIII from mammalian cells carrying the gene therefor, comprising culturing said mammalian cells in medium free of plasma-derived protein and supplemented with divalent metal ions, including $Cu^{2+}$ and $Zn^{2+}$, and optionally in the presence of $Ca^{2+}$ and $Mn^{2+}$ ions.

26 Claims, 6 Drawing Sheets

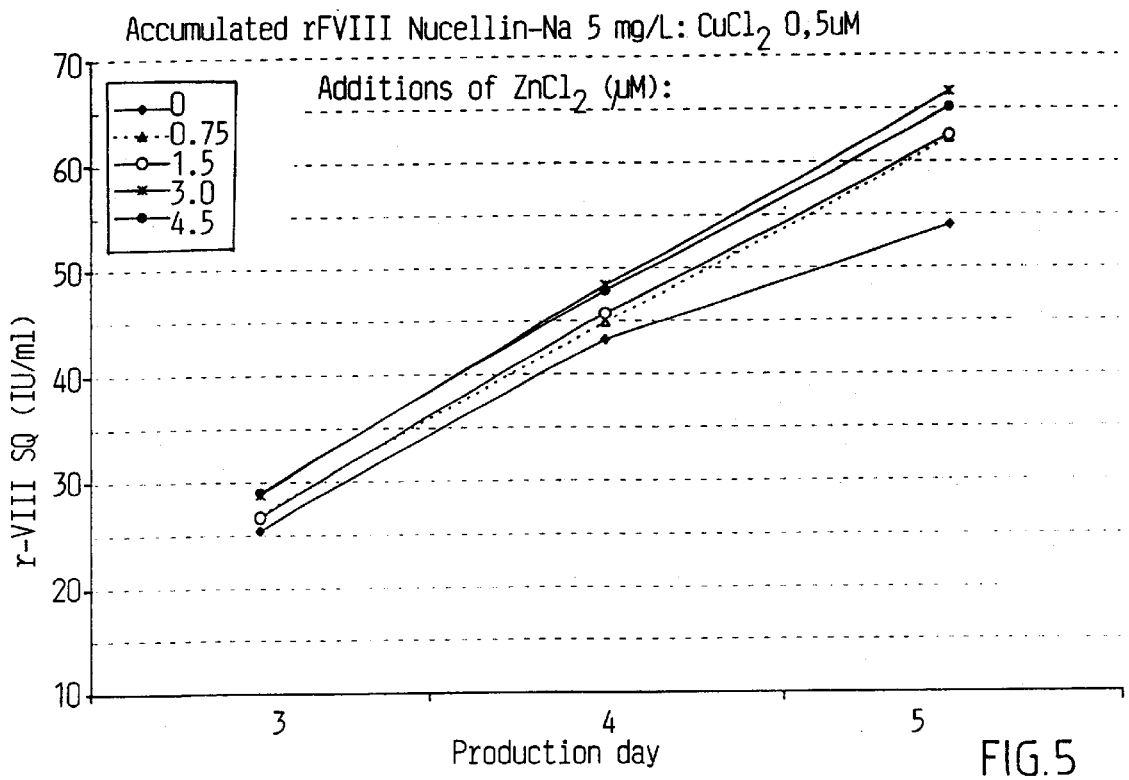
FIG. 5
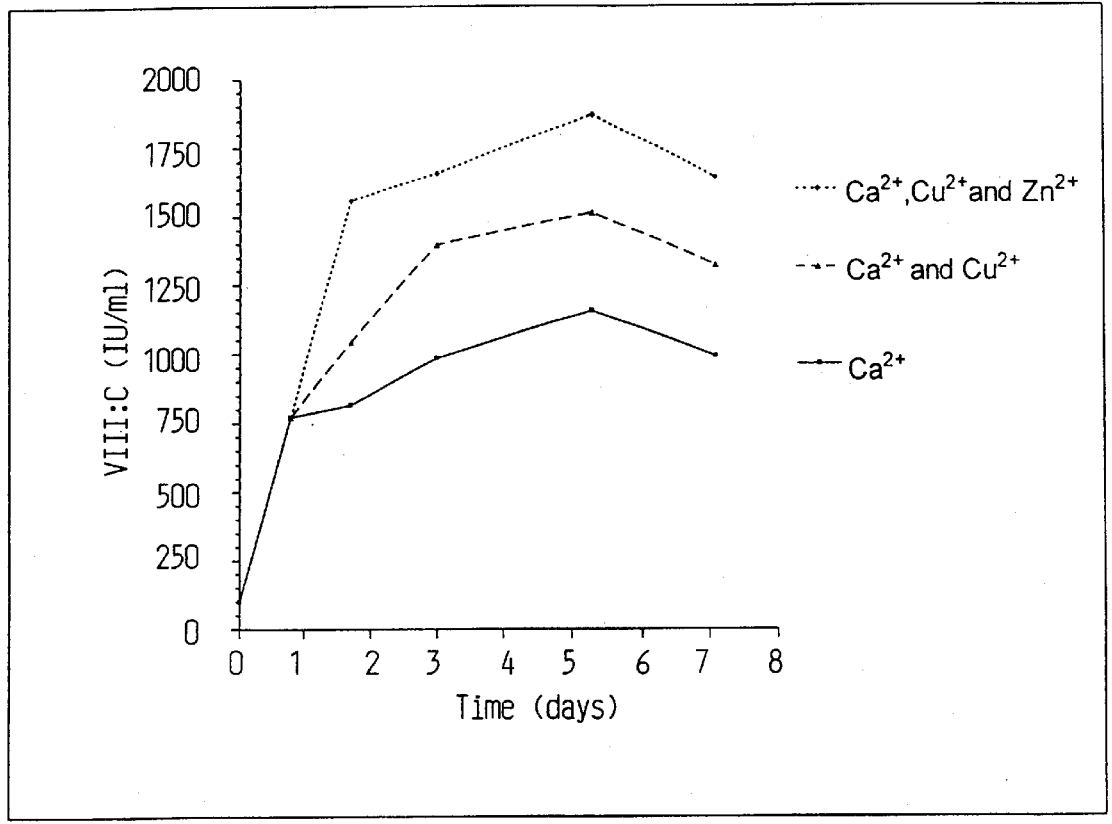
FIG. 6 Reconstitution of FVIII activity.

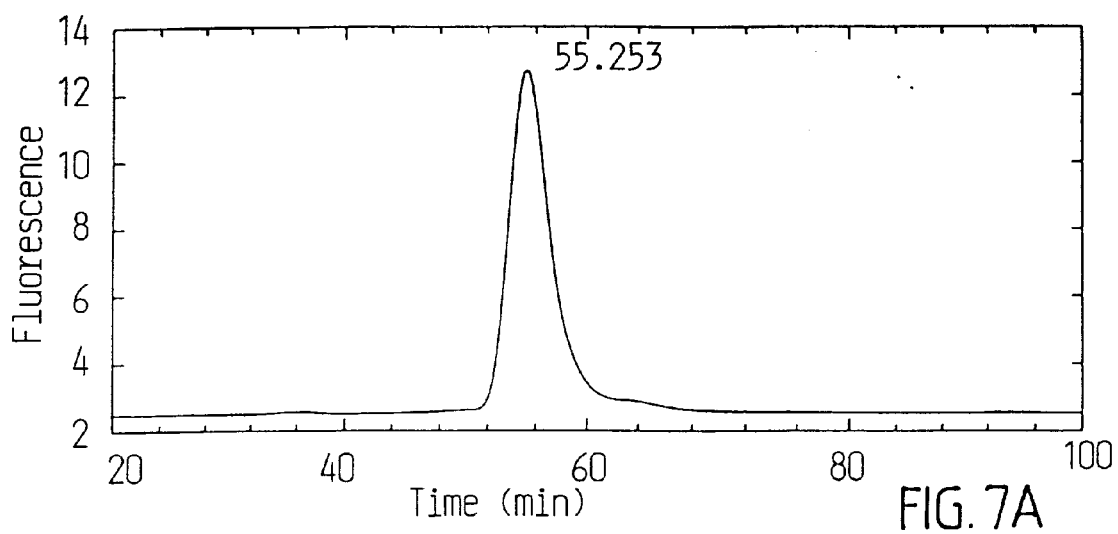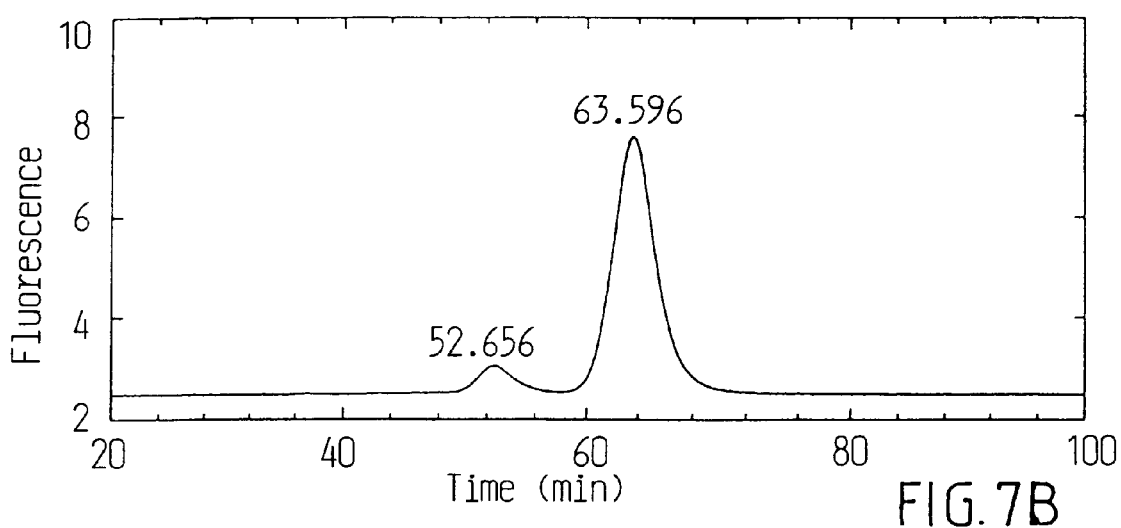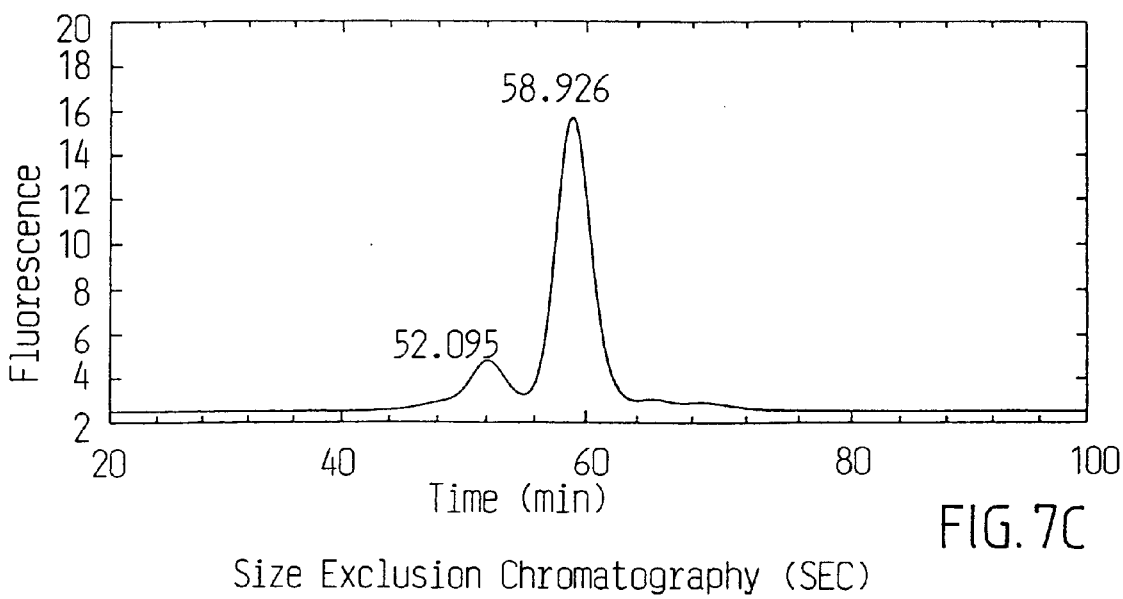
Size Exclusion Chromatography (SEC)

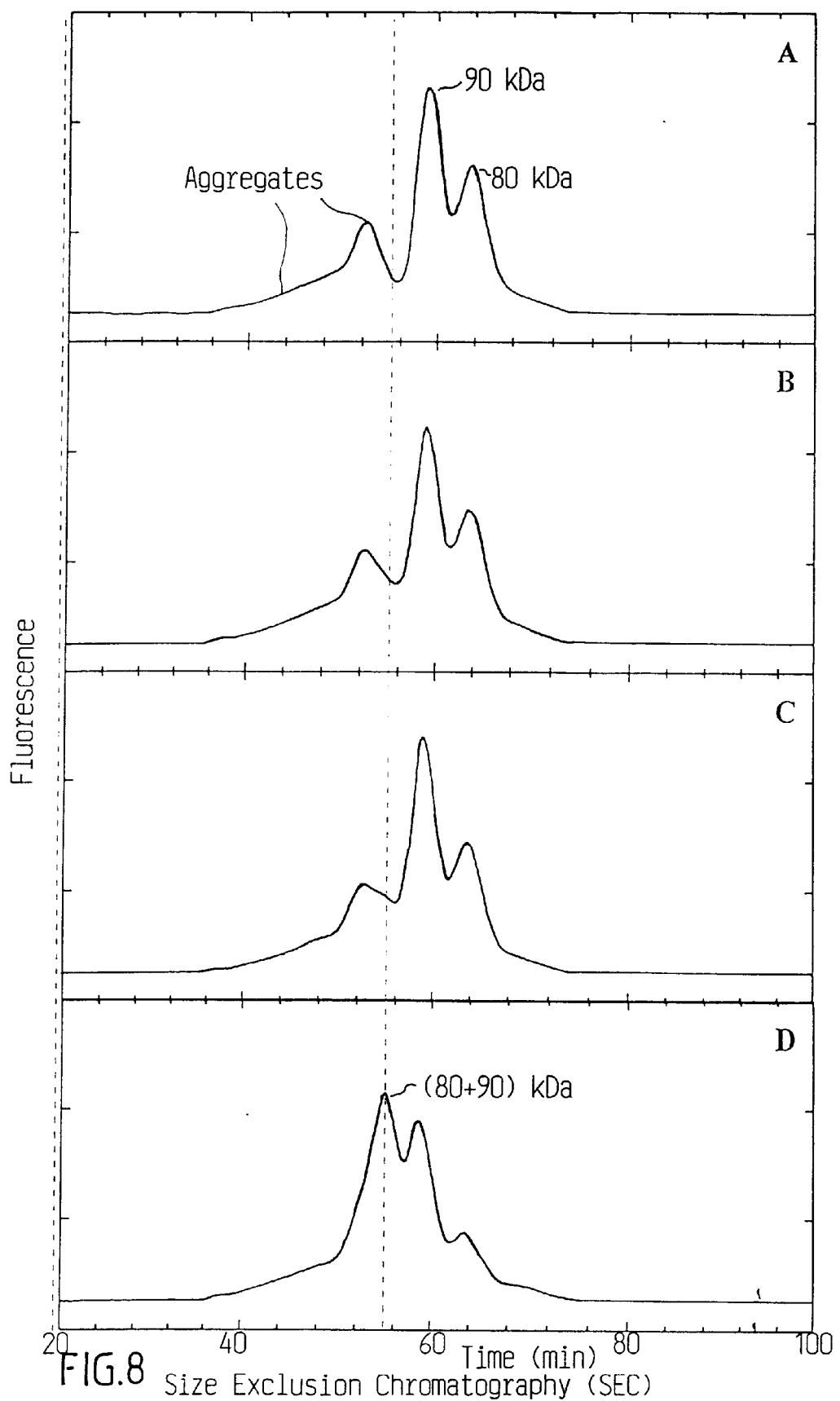
FIG.8 Size Exclusion Chromatography (SEC)

STABLE FACTOR VIII COMPOSITIONS

CROSS REFERENCE TO RELATED APPLICATIONS

This application claims priority from Swedish Patent Application No. 9902685-8, filed Jul. 13, 1999, Swedish Patent Application No. 0001743-4, filed May 11, 2000, and U.S. Provisional Patent Application Serial No. 60/146,828, filed Aug. 2, 1999. These applications are incorporated herein by reference in their entirety.

TECHNICAL FIELD

The present invention relates to pharmaceutical compositions comprising coagulation Factor VIII, said compositions being stabilized, without the addition of albumin, by divalent metal ions, in particular $Zn^{2+}$. The invention also relates to a method for production of recombinant Factor VIII, comprising culturing said mammalian cells in medium free of plasma-derived protein and supplemented with divalent metal ions, in particular $Zn^{2+}$.

BACKGROUND ART

Classic hemophilia or hemophilia A is the most common of the inherited bleeding disorders. It results from a chromosome X-linked deficiency of blood coagulation Factor VIII, and affects almost exclusively males with an incidence of between one and two individuals per 10,000. The X-chromosome defect is transmitted by female carriers who are not themselves hemophiliacs. The clinical manifestation of hemophilia A is an abnormal bleeding tendency and before treatment with Factor VIII concentrates was introduced, the mean life span for a person with severe hemophilia was less than 20 years.

The use of concentrates of Factor VIII from plasma has considerably improved the situation for the hemophilia patients. The mean life span has increased extensively, giving most of them the possibility to live a more or less normal life. However, there have been certain problems with the plasma derived concentrates and their use, the most serious of which have been the transmission of viruses. Although various virus inactivation methods have been developed, it appears likely that it will be impossible to render plasma-derived Factor VIII completely free from the risk of viral transmission.

The development of recombinant Factor VIII products, as opposed to plasma-derived Factor VIII, would apparently involve a lower risk for transmission of infectious agents. The molecular cloning of DNA coding for human Factor VIII was independently reported by research groups from Genentech Inc. (Gitschier, J. et al. (1984) Nature 312, 326–330; Wood, W. I. et al. (1984) Nature 312, 330–337; Vehar, G. A. et al. (1984) Nature 312, 337–342) and from Genetics Institute Inc. (Toole, J. J. et al. (1984) Nature 312, 342–347). Factor VIII mRNA encodes a precursor protein of 2351 amino acids including a 19 amino acid signal peptide; thus the mature Factor VIII protein is 2332 amino acids long. The amino acid sequence predicted a domain structure consisting of a triplicated A domain, a unique B domain and a duplicated C domain arranged in the order A1:A2: B:A3: C1: C2. During coagulation the B domain is removed by thrombin activation of the molecule and its function is unknown.

Characterization studies of recombinant human Factor VIII (Eaton, D. L. et al. (1987) J. Biol. Chem. 262, 3285–3290) showed that it is structurally and functionally very similar to plasma-derived Factor VIII. In plasma prepared in the presence of protease inhibitors, Factor VIII appeared as a complex of one heavy chain between 90–200 kDa (domains A1 and A2, with variable extensions of the B domain), in combination with one 80 kDa light chain (domains A3:C1:C2) (Andersson, L. O. et al. (1986) Proc. Natl. Acad. Sci. U.S.A. 83, 2979–2983). The chains could be dissociated by EDTA, indicating that they are held together by metal ions. The C-terminal part of the heavy chain, containing the heavily glycosylated B-domain, is shown to be very sensitive to proteolytic attack by serine proteases.

Even in recombinant Factor VIII products there still remains a small but definite potential risk for transmission of infectious agents. Human albumin is a potential source of infection as it is used to stabilize the present recombinant Factor VIII products Kogenate® and Recombinate® (For a review, see Roddie, P. H. & Ludlam, C. A. (1997) Blood Reviews 11, 169–177). The presence of human parvovirus B19 DNA in recombinant, albumin containing Factor VIII products has been reported (Eis-Hübinger, A. M. et al. (1996) Thrombosis and Haemostasis 76, p.1120).

A recombinant Factor VIII lacking the B domain, (r-VIII SQ), is produced by Pharmacia & Upjohn (for a review, see Berntorp, E. (1997) Thrombosis and Haemostasis 78, 256–260; see also EP-A-0506757). The r-VIII SQ protein, which consists of a 90 kDa heavy chain (domains A1:A2) and the 80 kDa light chain (domains A3:C1:C2), connected by a linker peptide, is produced in CHO cells cultured in medium which is serum-free but contains human serum albumin. Albumin is not required for stabilization of the final product, which instead contains Polysorbate 80, a non ionic detergent that has been shown to prevent activity losses caused by surface adsorption (cf. WO 94/07510).

A divalent metal ion is essential for the structural integrity and cofactor function of Factor VIII. However, little information is available regarding how metal ions fulfill these roles. Various models for the metal-dependent association of Factor VIII subunits have been proposed. Factor VIII has been suggested to circulate in normal plasma as a calcium-linked protein complex (Mikaelsson, M. et al. (1983) Blood 62, 1006–1015). Factor VIII activity has been reconstituted by recombining the subunits in the presence of Ca(II) or Mn(II) (Fay, P. J. (1988) Arch. Biochem. Biophys. 262, 525–531). Other authors have proposed that a copper atom is located between the A1 and A3 domains and is a structural prerequisite to maintain the association between the heavy and light chains (Bihoreau, N. et al. (1994) Eur. J. Biochem. 222, 41–48; Pan, Y. et al. (1995) Nature Structural Biology 2, 740–744; Pemberton, S. et al. (1997) Blood 89, 2413–2421).

U.S. Pat. No. 5,804,420 (Chan et al./Bayer Corporation) discloses a method for production of recombinant Factor VIII, comprising culturing host cells in medium free of plasma-derived protein and supplemented with polyols and copper ions.

By addition of $Ca^{2+}$ ions and increase in the ionic strength when formulating r-VIII SQ as a solution it has been possible to reach a storage stability of a few months at +7° C. (Fatourus, A. et al. (1997) Int. J. Pharm. 155, 121–131). Further improvement has been achieved by addition of large amounts of sucrose (Fatouros, A. et al. (1997) Pharm. Res. 14(12), 1679–1684). However, none of the formulations with a reasonably elevated osmolality had an acceptable long-term storage stability.

Replacement therapy with intravenous injection of Factor VIII is usually given in the patient's home by a parent or the patient himself. Prior to administration the lyophilized Factor VIII concentrate has to be reconstituted under aseptic conditions, which is inconvenient and time-consuming. As a result there is often a substantial delay between the onset of bleeding symptoms and the treatment. This delay may increase the risk of chronic progressive joint damage.

A stable, ready-to-use solution of Factor VIII would be of great benefit to the patients. A convenient dosage form is expected to enhance therapy compliance, i.e. a more timely treatment, thereby reducing the likelihood of developing joint destruction. Besides the obvious advantages to the patients, elimination of the lyophilization step would simplify the manufacturing process and reduce both production and investment costs. At present there are no ready-to-use solutions of Factor VIII available. The stability of Factor VIII in solution is normally very poor; the same is true for B-domain deleted Factor VIII. Consequently, there is a need for a stable, ready-to-use composition of Factor VIII in order to enhance therapy compliance, and to simplify the manufacturing process.

Further, for plasma-derived Factor VIII, the current use of citrate anticoagulant reduces the levels of free divalent ions in the source plasma. For recombinant Factor VIII the yield in the cell culture process may be dependent on optimum concentrations of divalent metal ions in the cell culture medium. Thus there is also a need for improvements in the process of purification of Factor VIII, including the cell cultivation step in the production of recombinant Factor VIII.

BRIEF DESCRIPTION OF THE DRAWINGS

FIG. 5: Recombinant Factor VIII (r-VIII SQ) activity (IU/ml) in cell culture supplemented with combinations of $Zn^{2+}$ and $Cu^{2+}$.

FIG. 6: Reconstitution of activity (IU/ml) of EDTA treated pure recombinant Factor VIII (r-VIII SQ) by the use of combinations of $Zn^{2+}$, $Cu^{2+}$ and $Ca^{2+}$ (Example 4).

FIG. 7: Size Exclusion Chromatography (SEC) of samples from the reconstitution experiments of Example 4, showing the elution patterns of intact r-VIII SQ, the isolated 80 kDa subunit and the isolated 90 kDa subunit.

FIG. 8: Size Exclusion Chromatography (SEC) of samples from the reconstitution experiments of Example 4, showing the elution patterns after mixing free 80 and 90 kDa subunits with $Ca^{2+}$ or $Ca^{2-}$ combined with $Cu^{2+}$ or $Ca^{2-}$ combined with $Zn^{2+}$ or a combination of $Ca^{2+}$, $Cu^{2+}$ and $Zn^{2+}$.

DISCLOSURE OF THE INVENTION

Figure 1A:
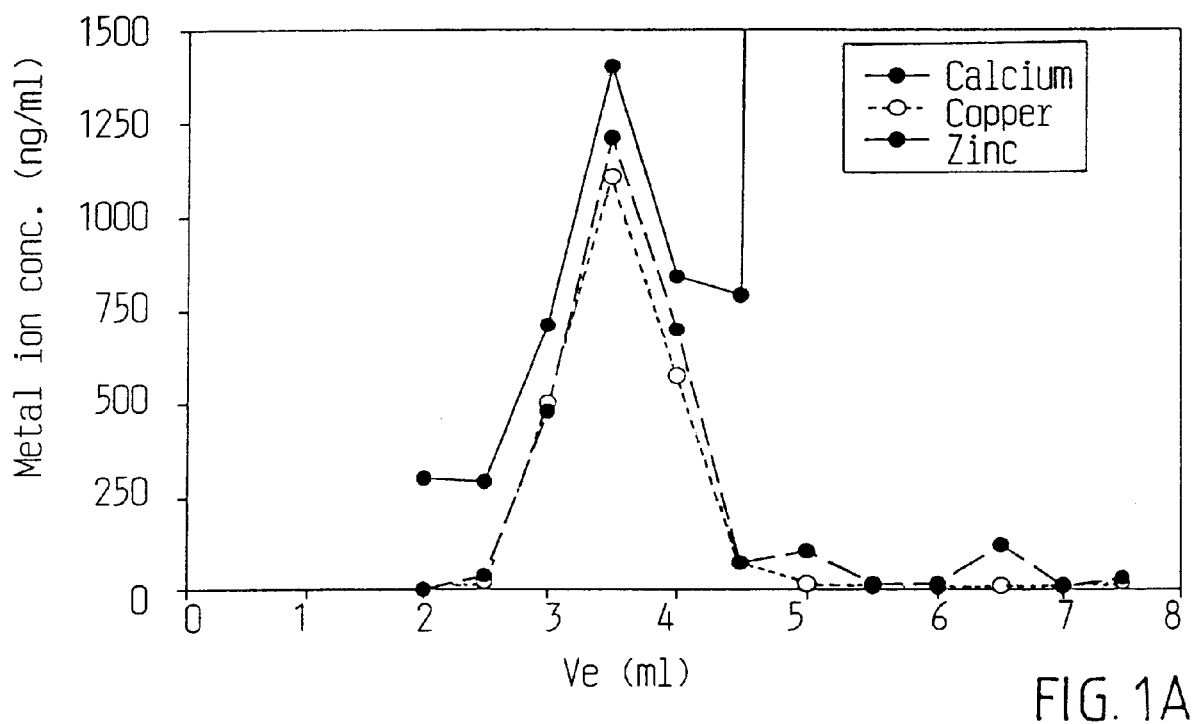
FIG. 1: Determination of metal ion content (A) and Factor VIII activity (B) after gel filtration of recombinant Factor VIII (r-VIII SQ).

Surprisingly, Factor VIII has been found to contain three different metal ions, namely $Ca^{2+}$, $Cu^{2+}$ and $Zn^{2+}$, one mole of each per mole of Factor VIII. In particular, the presence of zinc ions in Factor VIII has not earlier been reported or suggested. This finding enables improvements in the stability and yield of Factor VIII during manufacturing of both plasma-derived and recombinant Factor VIII.

For both plasma-derived and recombinant Factor VIII, the presence of $Zn^{2+}$ and $Cu^{2+}$, optionally in combination with $Ca^{2+}$ and/or $Mn^{2+}$ at optimum concentrations, has advantageous effects on the stability and yield of Factor VIII during both purification and final formulation. Finally, the long-term storage stability of Factor VIII, especially in aqueous solutions, is improved by the addition of $Zn^{2+}$ and $Cu^{2+}$ and optionally in combination with $Ca^{2+}$ and/or $Mn^{2+}$ and in adequate amounts.

Consequently, in a first aspect this invention provides a pharmaceutical composition comprising Factor VIII and divalent metal ions, said divalent metal ions including $Zn^{2+}$ ions and $Cu^{2+}$ ions, and optionally in combination with $Ca^{2+}$ and/or $Mn^{2+}$, wherein said Factor VIII is stable without the addition of albumin.

The said divalent metal ions are present in amounts sufficient for preservation of Factor VIII activity during storage without albumin for at least 6 months. Preferably, the said $Ca^{2+}$ ions are included in a calcium salt, such as calcium gluconate or preferably calcium chloride, present in a concentration of at least 0.1 mM, such as at least about 0.5 mM. If $Mn^{2+}$ is included in the composition of the present invention, the concentration thereof can be at least 0.1 mM, such as at least about 0.5 mM. The amounts of $Zn^{2+}$ and $Cu^{2+}$ ions required, when added as chlorides or possibly other salts, is dependent on the choice of excipients, especially the buffering substance. Histidine, phosphate and other buffers, normally used in protein formulations, have the disadvantage of being metal ion chelators. Therefore the $Zn^{2+}$ and $Cu^{2+}$ ions have to be added in amounts high enough to result in the presence of free metal ions in the solution. Hence, the total concentration of zinc and copper salts needed may vary between 0.1 $\mu$M and 1 mM.

The composition according to the invention is an aqueous solution ready for use, or alternatively, dried and reconstituted before use. In the compositions according to the invention, Factor VIII is present in a concentration from 50 to 50,000 IU/ml. Factor VIII can be derived from human plasma, or a full-length or a deletion derivative of recombinant Factor VIII, in particular the deletion derivative identified as r-VIII SQ.

The purification of Factor VIII from human plasma can be carried out by methods well known in the art, e.g. as described by Andersson, L. O. et al. (1986) Proc. Natl. Acad. Sci. U.S.A. 83, 2979–2983. The production of recombinant Factor VIII can be carried out by methods well known in the art, see e.g. Wood, W. I. et al. (1984) Nature 312, 330–337; or Toole, J. J. et al. (1984) Nature 312, 342–347. Factor VIII cDNA assembled into an efficient transcription unit can be introduced into a suitable host organism for expression of the Factor VIII protein. Preferably this organism should be an animal cell-line of vertebrate origin in order to ensure correct post-translational modifications. A preferred example of cell-lines that can be used is Chinese Hamster Ovary (CHO) cells. The recombinant Factor VIII protein, which accumulates in the medium of the cultured cells, can be concentrated and purified by a variety of biochemical methods, including methods utilizing differences in size, charge, solubility, hydrophobicity, specific affinity, etc. between the recombinant Factor VIII and other substances in the conditioned medium. The present invention includes improved processes for purification of Factor VIII, either plasma-derived or recombinant, wherein an optimal concentration of divalent metal ions is used.

The term "deletion derivative of recombinant Factor VIII" is defined as one or more polypeptide chains having Factor VIII activity, derived from full-length Factor VIII polypeptide by deleting one or more amino acids. Preferably, the said deletion derivative is devoid of most of the B-domain, but retains parts of the amino-terminal and carboxy-terminal sequences of the B-domain that are essential for in vivo proteolytic processing of the primary translation product into two polypeptide chains. The production of such a Factor VIII deletion derivative, identified as "r-VIII SQ" is described in WO 91/09122. The term "r-VIII SQ" is defined as a polypeptide chain derived from full-length Factor VIII and lacking amino acids 743 through 1636.

The Factor VIII protein, either recombinant or plasma-derived, can be formulated into the pharmaceutical compositions according to the present invention by methods well known in the art, see e.g. WO 94/07510. The Factor VIII protein may be dissolved in conventional physiologically compatible aqueous buffer solutions to which there may be added, optionally, pharmaceutical adjuvants and/or carriers.

The composition according to the invention can preferably comprise a non-ionic surfactant. Compositions comprising Factor VIII and a non-ionic surfactant as a stabilizer are disclosed in WO 94/07510. The non-ionic surfactant is preferably chosen from block co-polymers such as a poloxamer or polyoxyethylene (20) fatty acid ester, such as polysorbate 20 or polysorbate 80. The non-ionic surfactant should be present in an amount above the critical micelle concentration (CMC) (See Wan & Lee (1974) J. Pharm. Sci. 63,136). The composition according to the invention can additionally comprise sodium or potassium chloride in a concentration above 0.1 M. The composition can also additionally comprise an amino acid, e.g. L-histidine, at a concentration of at least 1 mM.

In a preferred form of the invention, the composition comprises the following ingredients:

(i) from 50 to 50,0000 IU/ml of recombinant Factor VIII;
(ii) at least 0.1 mM, preferably at least about 0.5 mM, of a calcium salt; such as calcium chloride;
(iii) at least 1 mM of L-histidine;
(iv) at least 0.1 M of sodium chloride;
(v) at least 0.01 mg/ml of a polyoxyethylene (20) fatty acid ester;
(vi) a zinc salt, such as zinc chloride, optionally in combination with a copper salt, such as copper chloride, in a total concentration from 0.1 $\mu$M to 1 mM.

Aqueous compositions according to the invention include compositions having a reduced concentration of oxygen and/or comprising antioxidants. Examples of suitable antioxidants are those selected from the group consisting of glutathione, acetylcysteine, and methionine. The preparation of oxygen-reduced aqueous solutions of Factor VIII is known from WO 94/26286. To the composition according to the invention, mono-or disaccharides or sugar alcohols, preferably sucrose, preferably in an amount above 100 mg/ml, can be added. Aqueous Factor VIII solutions having a reduced concentration of oxygen and/or comprising antioxidants, and wherein the solution in addition comprises a carbohydrate in a concentration of at least 350 mg/ml, are disclosed in WO 96/30041.

In another important aspect, the invention provides a cell culture medium for the production of recombinant Factor VIII comprising (i) a basal medium free of plasma-derived protein and (ii) divalent metal ions including $Cu^{2+}$ and $Zn^{2+}$ ions. Optionally, the said divalent metal ions additionally include $Ca^{2+}$ ions and/or $Mn^{2+}$ ions. Preferably, the amount of $Ca^{2+}$ and/or $Mn^{2+}$ ions is at least about 0.1 mM. The said basal medium can contain plasma-derived proteins or, alternatively, be free of plasma-derived proteins.

The amount of $Zn^{2+}$ ions in the said cell culture medium is preferably at least about 0.2 $\mu$M. The invention also includes a cell culture medium wherein the amount of $Zn^{2+}$ ions is at least about 0.5 $\mu$M or 1 $\mu$M. The concentration range of $Zn^{2+}$ ions is preferably from about 0.2 to about 10 $\mu$M. The invention also includes a cell culture medium wherein the amount of $Zn^{2+}$ ions is from about 0.2 to 5 $\mu$M; from 0.5 to 10 $\mu$M; from 0.5 to 5 $\mu$M; from 1 to 10 $\mu$M; and from 1 to 5 $\mu$M.

The concentration range of $Cu^{2+}$ ions in the said cell culture medium is preferably from about 0.05 to about 5 $\mu$M. The invention also includes a cell culture medium wherein the amount of $Cu^{2+}$ ions is from 0.05 to 2 $\mu$M; from 0.1 to 5 $\mu$M; and from 0.1 to 2 $\mu$M.

In a further aspect, the invention includes a method for production of recombinant Factor VIII from mammalian cells carrying the gene therefor, comprising culturing said mammalian cells in a cell culture medium according to the invention as defined above.

EXAMPLES

The invention will now be further described by the following examples, which are not to be construed as limiting the invention in any way.

Example 1

Determination of Metal Content in Factor VIII

A preparation (HIC-eluate) containing r-VIII SQ was obtained from the butyl-Sepharose step in the purification process as described by Smeds A-L. et al. (1995) Thrombosis and Haemostasis 73, 1015. A plasma-derived Factor VIII (pd-FVIII) preparation was purified essentially as described by Andersson, L. O. et al. (1986) Proc. Natl. Acad. Sci. U.S.A. 83, 2979–2983, and contained Factor VIII molecules of 185 to 280 kDa, with a calculated mean mass of 220 kDa. Both preparations were stored at −70° C. Special precautions were taken in order to minimize the risk of metal ion contamination of the samples during preparation. Extra pure reagents, with only trace amounts of metal ions were used. Only vessels, tubes, tips etc. made out of plastic were used and were washed with 10% $HNO_3$ and water before use.

Figure 1B:
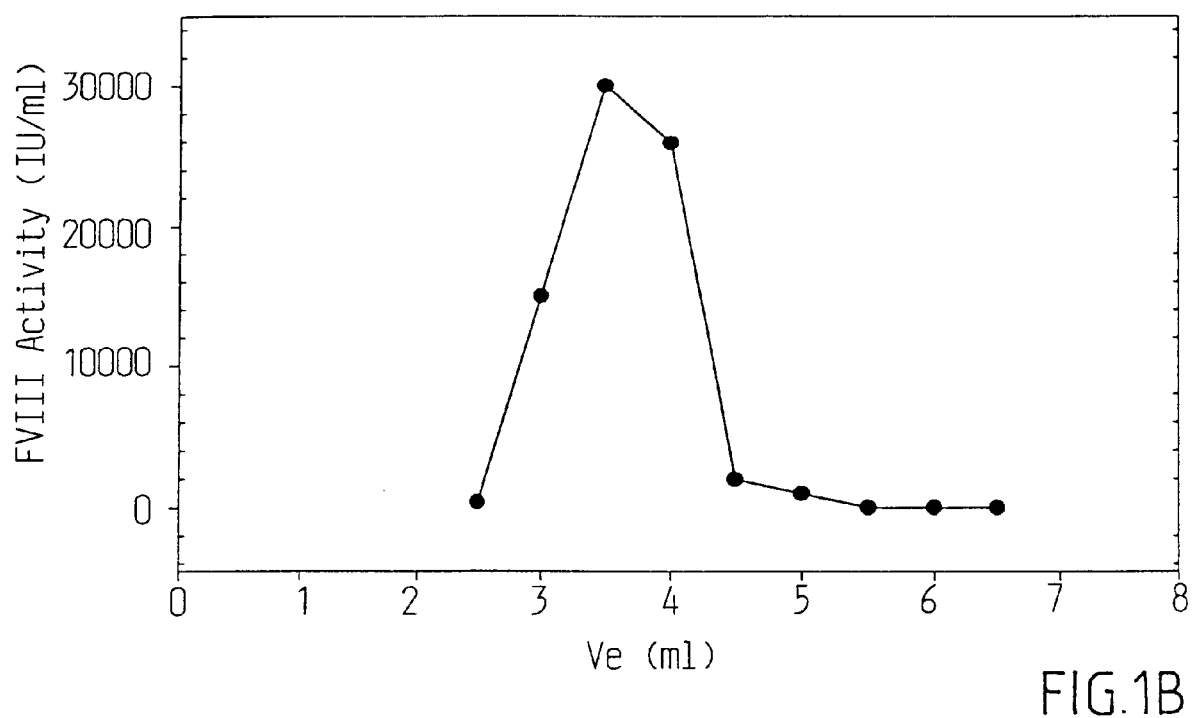
Figure 2A:
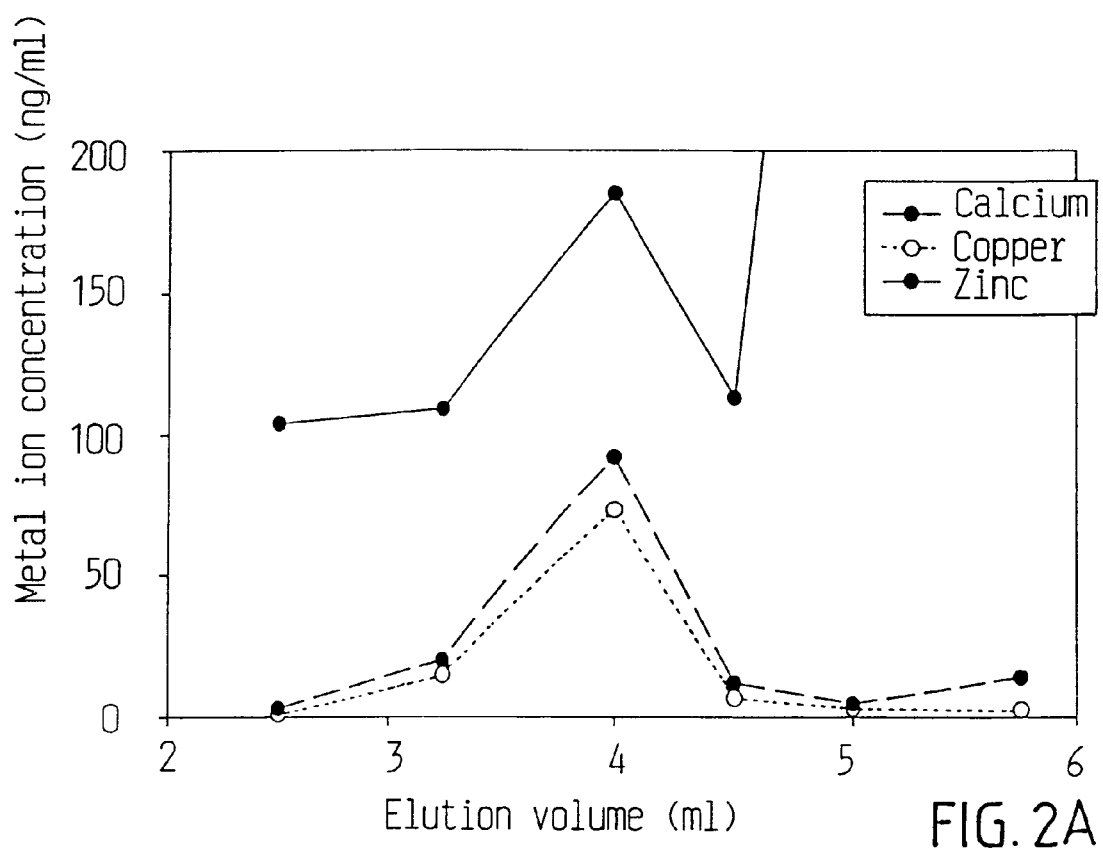
FIG. 2: Determination of metal ion content (A) and Factor VIII activity (B) after gel filtration of plasma-derived Factor VIII.
Figure 2B:
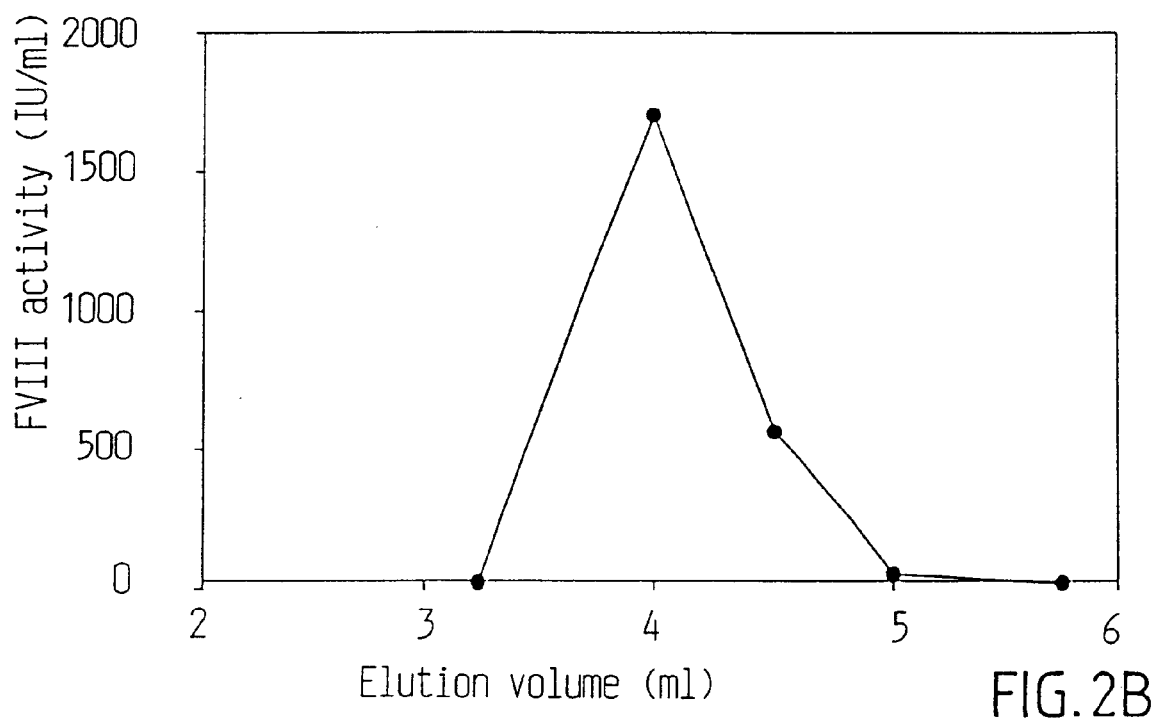

The buffer of the Factor VIII samples was changed to 20 mM Tris (pH 7.4), 0.3 M NaCl by gel filtration, performed at room temperature. Pre-packed columns with Sephadex G-25®, medium grade (PD-10, Amersham Pharmacia Biotech, Uppsala, Sweden) were used. The columns were washed with 25 ml of 0.1 M HCl, followed by 50 ml of distilled water prior to equilibration with 25 ml of buffer. Thereafter, 1 ml of a Factor VIII sample was applied to the column and fractions were collected during elution. Collected fractions from gel filtration of r-VIII SQ (FIG. 1) or pd-VIII (FIG. 2) were analyzed for metal ions (panels A) and Factor VIII activity (panels B).

Factor VIII activity was determined by a two-stage method using a chromogenic substrate, essentially as described by Rosén (1984) J. Haematol. Vol. 33, Suppl. 40, 139–145; and by Carlebjörk et al. (1987) Thrombosis Research Vol. 47, 5–14. Metal analysis of Factor VIII samples was performed by Svensk Grundämnesanalys AB (SGAB). The methods used were High-Resolution Inductively Coupled Plasma Mass Spectroscopy (HR-ICP-MS) and Inductively Coupled Plasma Atomic Emission Spectroscopy (ICP-AES). The metal content in the buffer was subtracted when calculating the metal content of Factor VIII.

Samples from the fractions showing highest Factor VIII activity and metal content were analyzed by amino acid analysis for determination of protein concentration. Molecular masses of 165,305 Da for r-VIII SQ, and 220,000 Da for pd-FVIII, were used for calculation of molar concentrations. Molar ratios of metal ions and Factor VIII were calculated. The results, shown in Table I, indicate that both r-VIII SQ and pd-FVIII contained 1 mole of copper, calcium and zinc per mole of Factor VIII. The ratios for calcium could be overestimated due to a high background concentration of calcium in the buffer.

The methods used for metal analysis also allowed quantitation of magnesium, manganese, nickel, iron, cobalt, strontium, etc., but none of these metal ions were detected in the Factor VIII preparations.

TABLE I

Molar ratios (mol of metal ion per mole of Factor VIII)

| Metal ion | r-VIII SQ | pd-FVIII |
|---|---|---|
| $Ca^{2+}$ | 1.3 | 1.4 |
| $Cu^{2+}$ | 0.8 | 1.0 |
| $Zn^{2+}$ | 0.9 | 1.0 |

Example 2

Stability of Factor VIII Compositions in the Presence of Divalent Metal Ions

The stability of Factor VIII compositions according to the invention is tested by preparing compositions having various amounts of divalent metal ions $Ca^{2+}$, $Zn^{2+}$ and $Cu^{2+}$. After storage for a suitable time period, Factor VIII activity is determined by methods known in the art, e.g. as described by Rosén (1984) J. Haematol. Vol. 33, Suppl. 40, 139–145; and by Carlebjörk et al. (1987) Thrombosis Research Vol. 47, 5–14. The results indicate that Factor VIII compositions according to the invention, comprising an optimal concentration of divalent metal ions have advantageous properties with regard to long-term stability.

Example 3

Effect of Divalent Metal Ions During Cultivation of a Cell-line Expressing Recombinant Factor VIII 3.1. Materials and Methods A clonal variant of the Chinese hamster ovary cell (CHOTf677:16 SQ) engineered to express rFVIII (see Lind, P. et al. (1995) Eur. J. Biochem 232, 19–27) was used in all experiments. The cells were cultivated as suspension cultures in spinner flasks using a proprietary, serum free culture medium containing recombinant insulin (Nucellin-Zn™ or Nucellin-Na™, Eli Lilly). It should be noted that the concentration of $Zn^{2+}$ in the cultivation medium was from 0.3–0.9 μM, and that the concentration of $Ca^{2+}$ was 0.3 mM throughout the whole experiment (including the control).

A small-scale test method was established for screening of medium component additives. A shaker table AgCell (BeLach Bioteknik AB) equipped with holders for 50 ml Falcon tubes was used for keeping the cells in suspension. The culture volume in the tubes was 5 ml and the cell density $1.5 \times 10^6$ cells per ml. The medium was changed after 3 days by centrifugation, 950 rpm (182×g) for 5 minutes.

The cultures were incubated on the shaker table, at a speed of 130–140 shakes per min and monitored for 5 days. Cell density, viability and r-VIII SQ concentration was determined at days 3, 4 and 5. Cell densities were typically around $1 \times 10^6$ cells per ml and viability higher than 90% at the end of the experiments. Factor VIII concentration was quantitated by a chromogenic assay, Coatest® (Chromogenix). Cf. Rosén (1984) J. Haematol. Vol. 33, Suppl. 40, 139–145; and Carlebjörk et al. (1987) Thrombosis Research Vol. 47, 5–14.

3.2. Results

Controls

The positive controls received 30 mg/L Nucellin-Zn. The average accumulated yield for the positive controls was 56 IU/ml r-VIII SQ after the 5 production days (Table II). Omitting insulin all together resulted in poor survival and viability and as a consequence poor productivity. The accumulated values reached without Nucellin-Zn were 8.5 IU/ml.

All concentrations tested in a titration experiment with Nucellin-Zn, (1, 5, 10, 20 and 30 mg/L final concentrations) resulted in good survival of the cells. The lowest concentration tested (1 mg/L) was clearly not sufficient to support also good productivity. The titration showed a dose-response correlation; the more Nucellin-Zn, the higher the total accumulated yield. The highest concentration (30 mg/L) gave a 62% increase compared to 1 mg/L.

To be able to compare metal additions to the culture medium, an insulin analogue (Nucellin-Na, Eli Lilly) containing sodium instead of zinc was used. Increasing concentrations of Nucellin-Na did not result in the clear dose-response effect seen with Nucellin-Zn. The difference in accumulated product between the lowest (1 mg/L) and the highest (30 mg/L) concentration tested was 22%.

Increasing Amounts of $Zn^{2+}$

Increasing amounts of Nucellin-Na (1, 5 and 20 mg/L) were combined with increasing levels of $ZnCl_2$ (0.15, 0.75, 1.5, 3.0 and 4.5 μM) for assessing the $Zn^{2+}$ effect on productivity.

Figure 3:
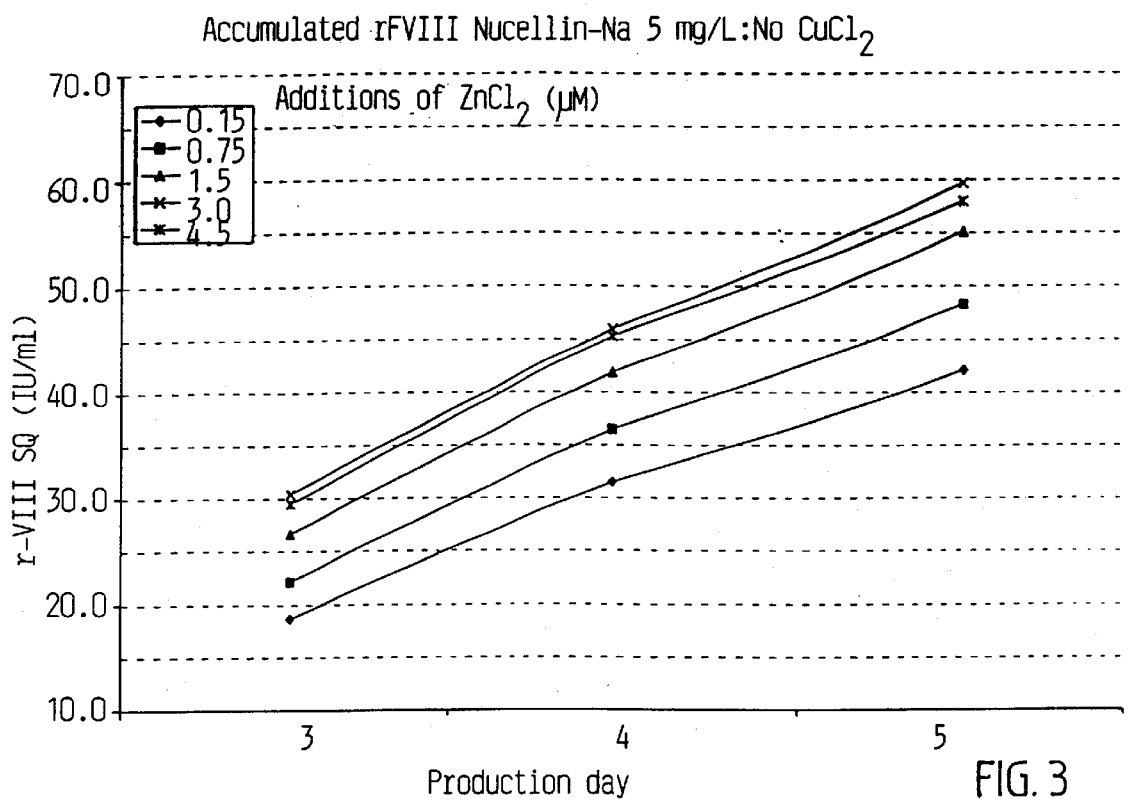
FIG. 3: Recombinant Factor VIII (r-VIII SQ) activity (IU/ml) in cell culture supplemented with various amounts of $Zn^{2+}$.

In all Nucellin-Na amounts tested, addition of $ZnCl_2$ gave a better product yield. Using 5 (see FIG. 3) or 20 mg/L Nucellin-Na in combination with $ZnCl_2$ resulted in an accumulated product yield of 57–58 IU/ml. These results correspond to the yield achieved with the positive control (Nucellin-Zn at 30 mg/L). Compared to controls that did not receive $ZnCl_2$ but only Nucellin-Na at 5 mg/L, the total accumulated values of 57 IU/ml corresponded to an increase of 14% (see Table II). Since an increase above 5 mg/L Nucellin-Na did not lead to higher product titers, this concentration was chosen for further experiments.

Increasing Amounts of $Cu^{2+}$

Figure 4:
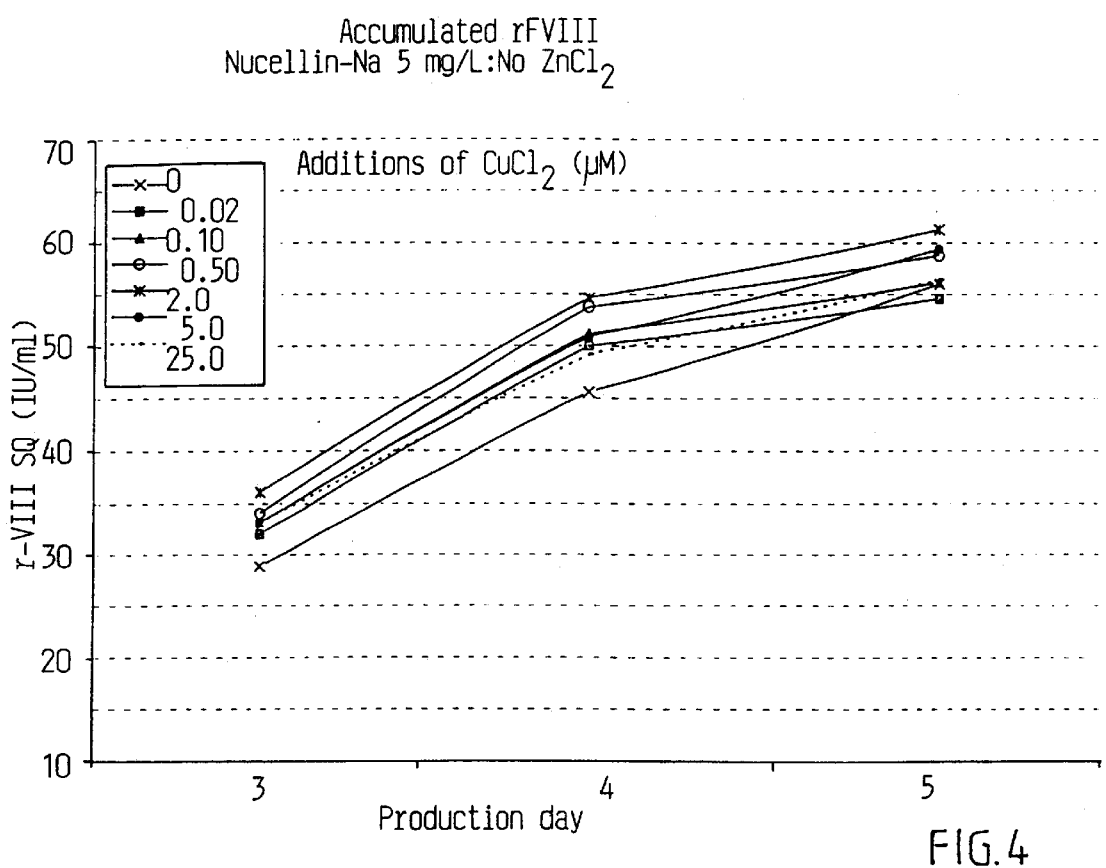
FIG. 4: Recombinant Factor VIII (r-VIII SQ) activity (IU/ml) in cell culture supplemented with various amounts of $Cu^{2+}$.

Supplementing the medium with increasing amounts of $CuCl_2$ (0.02, 0.1, 0.5, 2 and 5 μM) resulted in an accumulated product yield of 61 IU/ml (FIG. 4 and Table II). This was an increase of 22% compared to the internal control.

Combinations of $Zn^{2+}$ and $Cu^{2+}$

With combinations of $ZnCl_2$ (0.75, 1.5, 3.0 and 4.5 μM) and $CuCl_2$ (0.1 or 0.5 μM), the total accumulated levels of product increased with 28% (64 IU/ml) compared to the internal control (Table II). Consequently, a synergistic effect of $Zn^{2+}$ and $Cu^{2+}$ could be observed. FIG. 5 shows the results obtained with 0.5 μM $CuCl_2$.

TABLE II

Factor VIII activity (IU/ml); 5 day accumulated titer

|  | IU/ml | % of internal control |
|---|---|---|
| Positive control: Nucellin-Zn (30 mg/L) | 56 | 113 |
| Internal control: Nucellin-Na (5 mg/L) | 50 | 100 |
| Nucellin-Na (5 mg/L) + ZnCl$_2$ (0.75 to 4.5 μM) | 57 | 114 |
| Nucellin-Na (5 mg/L) + CuCl$_2$ (0.5 to 5 μM) | 61 | 122 |
| Nucellin-Na (5 mg/L) + CuCl$_2$ (0.1 or 0.5 μM) + ZnCl$_2$ (0.75 to 4.5 μM) | 64 | 128 |

Example 4

Influence of Calcium, Copper and Zinc on the Re-association of Separated, Metal-ion Depleted Subunits and On Reconstitution of FVIII Activity

Materials and Methods
(i) Dissociation of Subunits of FVIII

The r-VIII SQ preparation was material from the butyl-Sepharose step in the purification process, as described in Example 1. The heavy and the light chain of r-VIII SQ was dissociated by incubation of r-VIII SQ with the chelating agent EDTA. The factor VIII activity was lost in parallell. Equal volumes of r-VIII SQ and 0.5 M EDTA, 100 mM Tris, pH 7.4, were mixed and left in room temperature for 6 h. EDTA-metal ion complexes were removed by chromatography on a Sepharose G-25 column in 20 mM Tris, 0.3 M NaCl, 0.01% Tween 20, pH 7.5.

(ii) Purification of Separate Subunits of FVIII

The r-VIII SQ preparation was material from the butyl-Sepharose step in the purification process, as described in Example 1. Equal volumes of r-VIII and 0.5 M EDTA, 100 mM Tris, pH 8.0, were mixed and left overnight at 5° C. The mixture was then applied onto an affinity column, with monoclonal antibodies directed towards the 80 kDa chain of FVIII. Free 80 kDa chain as well as the 170 kDa chain was bound to the column. The flow through, containing free 90 kDa chain was collected. The column was then eluted with 20 mM Tris, 50 mM CaCl2, 50% ethylene glycol, 0.02% Tween 80, pH 6.8. The protein containing fractions were collected, diluted 1:5 with the same buffer without ethylene glycol, and applied onto another affinity column, with monoclonal antibodies directed towards the 90 kDa chain. The 170 kDa chain was bound to the column. The flow through containing the 80 kDa chain was collected. Part of the flow through material was concentrated by ultrafiltration (PallFiltron filter, 30 k cut off). Protein concentration was determined either by amino acid analyses or by the Lowry method (Kit from SIGMA) using BSA as the standard.

(iii) Reassociation of FVIII Subunits and Reconstitution of Activity

The FVIII subunits were reassociated and FVIII activity was reconstituted by addition of metal ions. In all experiments, calcium chloride (c. 5 mM) was initally added. Then after incubation over night at room temperature, copper(II)chloride and/or zinc chloride, was added. The final molar ratio of Cu$^{2+}$ or Zn$^{2+}$/r-VIII SQ was 50–67. The mixture was further incubated for 1–5 days. Factor VIII coagulant activity was measured by a chromogenic substrate method as described in Example 1.

Results
a) Reconstitution of F VIII Activity After Incubation of r-VIII SQ with EDTA r-VIII SQ was treated according to description (i) in Material and Methods. At day 0, after 6 h incubation of r-VIII SQ with EDTA and removal of EDTA-metal ion complexes, calcium chloride (5 mM) was added to dissociated subunits of r-VIII SQ. After incubation at 22° C. for 1 day, the mixture was divided in 4 parts and diluted equally with buffer or solutions of copper(II)chloride and/or zinc chloride. The final protein concentration was 88 μg/ml. The molar ratio Cu$^{2+}$ and Zn$^{2+}$/r-VIII SQ was 50. The FVIII coagulant activity (VIII:C) was then measured once a day for 1 week. Full factor VIII activity was possible to achieve in these experiments. As is shown in FIG. 6, the highest FVIII activity was obtained with a combination of calcium, copper and zinc.

b) Reconstitution of the F VIII Active 80+90kDa Complex of r-VIII SQ from Separated and Isolated Subunits Separated and 90 and 80 kDa chains of r-VIII SQ, prepared accordingly to description (ii). in Material and Methods, were mixed (32 μg of each) in a buffer containing 5 mM calcium chloride (10 mM histidine, 10 mM Tris, 0.3 M NaCl, 5 mM CaCl$_2$, 0.02% Tween 80, pH 7.2). After incubation for 5 h at 22° C., the mixture was divided in four parts which were diluted equally with buffer or solutions of copper(II)chloride and/or zinc chloride. The final protein concentration was 197 μg/ml. The molar ratios of Cu$^{2+}$ and Zn$^{2+}$/r-VIII SQ was 60. After 19 h incubation at 22° C., the FVIII coagulant activity (VIII:C) of each sample was measured. Table III below shows the results obtained in this experiment.

TABLE III

| Sample no. | Metal ions added | VIII:C (IU/ml) | Specific activity (IU/μg) | Reconstituted activity* (%) |
|---|---|---|---|---|
| 1 | Calcium | 12 | 0.1 | 1 |
| 2 | Calcium, Copper | 120 | 0.6 | 4 |
| 3 | Calcium, Zinc | 280 | 0.9 | 6 |
| 4 | Calcium, Copper, Zinc | 732 | 3.7 | 26 |

*The reconstituted activity is expressed in percent of the specific activity of intact r-VIII SQ (14.3 IU/μg).

Samples from the reconstitution experiment described in Table III above were also analysed by SEC (size exclusion chromatography) on a Superdex-200 column. The results are shown in FIG. 7, where:

(A) denotes reference of r-VIII SQ, (80+90) kDa form;

(B) denotes isolated 80 kDa chain; and (C) denotes isolated 90 kDa chain.

Both preparations of subunits contain mostly monomeric chains, but also some aggregates. The retention times are indicated in the figure.

Samples from the reconstitution experiment described in Table III above were also analyzed by SEC (size exclusion chromatography) on a Superdex-200 column. The results are shown in FIG. 8, where:

(A) denotes sample containing Ca$^{2+}$;

(B) denotes sample containing Ca$^{2+}$ and Cu$^{2+}$;

(C) denotes sample containing Ca$^{2+}$ and Zn$^{2+}$; and (D) denotes sample containing Ca$^{2+}$, Cu$^{2+}$ and Zn$^{2+}$.

The position of the heavy chain, light chain as well as aggregates of these are indicated in (A). The position of the (80+90) kDa-dimer is indicated in (D). A dotted line is added to facilitate comparison of the different chromatograms.

Example 5

Effect of Divalent Metal Ions on Cell-free Supernatant from a Cultivation of a Cell Line Expressing Recombinant Factor VIII Cell-free supernatant, obtained from a cultivation of a clonal variant of the Chinese hamster ovary cell (CHOTf677:16 SQ) engineered to express rFVIII (see Lind, P. et al. (1995) Eur. J. Biochem 232, 19–27), was used for these experiments. The cell broth of this cultivation contained biologically active factor VIII, complex of the light 80 k chain and the heavy 90 k chain, and contained free light 80 k chains and free heavy 90 k chains. The cells were cultivated as suspension culture in a bioreactor using a an ordinary serum free cell culture medium containing 0.2 to 0.8 µM zinc contained in 5 mg/l recombinant insulin Nucellin-Zn™ (Nucellin-Zn™, Eli Lilly, which contains 0.3 to 1.08% of zinc), 0.07 µM ZnSO4.7H2O, 0.3 mM CaCl2 and 0.2% human serum albumin.

Cell-free supernatant was obtained by centrifuging cell broth from a suspension cultures at 950 rpm (182×g) for 5 minutes. Different combinations of MnCl2 and CuCl2 were supplemented to the cell-free supernatant distributed in different aliquots of 25 ml volumes in tubes. 0 or 2.5 mM MnCl2 was added to the supernatant and agitated. One hour later, 0.53, 1.58 or 9.5 µM CuCl2 was added to the supernatant and agitated. Then after 0, 1, 2.5, 5 or 23 hours factor VIII concentration was quantitated by a chromogenic assay, Coatest® (Chromogenix) in the tubes containing the metal-supplemented supernatant. Cf. Rosén (1984) J. Haematol. Vol. 33, Suppl. 40, 139–145; and Carlebjörk et al. (1987) Thrombosis Research Vol. 47, 5–14.

Control

The controls were aliquots of cell-free supernatant with the same agitation and waiting time manipulations as the metal-supplemented supernatant aliquots however without metal supplementation.

Results

An increase of up to 45% of biologically active FVIII, FVIII titre, could be obtained by adding MnCl2 and CuCl2 to the cell-free supernatant. Higher FVIII titre were obtained by adding a combination of MnCl2 and CuCl2 compared to adding CuCl2 only. The effect of adding metal ions was observed rapidly with a full effect obtained after 5 hours, see Table IV below. It should be noted that the concentration of $Zn^{2+}$ in the cultivation medium was from 0.3–0.9 µM, and that the concentration of $Ca^{2+}$ was 0.3 mM throughout the whole experiment (including the control).

TABLE IV

Effect of addition of CuCl2 and MnCl2 after 5 and 23 hours

| Conditions | $Mn^{2+}$ [mM] | $Cu^{2+}$ [µM] | FVIIIC* after 5 h [IU/ml] | FVIIIC after 5 h [%] | FVIIIC* after 23 h [IU/ml] | FVIIIC after 23 h [%] |
|---|---|---|---|---|---|---|
| control | 0 | 0 | 5.8 | 100 | 5,7 | 100 |
| a | 0 | 0.53 | 6.6 | 114 | 6,5 | 114 |
| b | 0 | 1.58 | 6.9 | 119 | 6,8 | 119 |
| c | 0 | 9.5 | 7.1 | 122 | 7,4 | 130 |
| d | 2.5 | 0.53 | 8.4 | 145 | 8,6 | 151 |
| e | 2.5 | 1.58 | 8.4 | 145 | 8,0 | 140 |
| f | 2.5 | 9.5 | 8.3 | 143 | 8,3 | 146 |

*FVIIIC is the factor VIII concentration quantitated by a chromogenic assay, Coatest ® (Chromogenix);

What is claimed is:

1. A pharmaceutical composition comprising Factor VIII and the divalent metal ions $Zn^{2+}$ and $Cu^{2+}$, wherein the Factor VIII is a dimer comprising a heavy chain of about 90 to 200 kilodaltons and a light chain of about 80 kilodaltons.

2. The composition according to claim 1, further comprising $Ca^{2+}$ ions.

3. The composition according to claim 1, further comprising $Mn^{2+}$ ions.

4. The composition according to claim 2, further comprising $Mn^{2+}$ ions.

5. The composition according to claim 1, wherein the $Zn^{2+}$ ions are present in a total concentration of from 0.1 µM to 1 mM.

6. The composition according to claim 2, wherein the $Ca^{2+}$ ions are included in a calcium salt present in a concentration of at least 0.1 mM.

7. The composition according to claim 1, wherein said divalent metal ions are present in amounts sufficient for preservation of Factor VIII activity during storage without albumin for at least 6 months.

8. The composition according to claim 1, which composition is an aqueous solution ready for use.

9. The composition according to claim 1, which composition is dried and adapted to be reconstituted before use.

10. The composition according to claim 1, wherein Factor VIII is present in a concentration of from 50 to 50,000 IU/ml.

11. The composition according to claim 1, wherein the Factor VIII is plasma-derived.

12. The composition according to claim 1, wherein the Factor VIII is full-length or a deletion derivative of recombinant Factor VIII.

13. The composition according to claim 12, wherein the Factor VIII is the deletion derivative identified as r-VIII SQ.

14. The composition according to claim 1, additionally comprising a non-ionic surfactant.

15. The composition according to claim 14, wherein the non-ionic surfactant is a polyoxyethylene (20) fatty acid ester present in a concentration of at least 0.01 mg/ml.

16. The composition according to claim 1, additionally comprising sodium or potassium chloride in a concentration above 0.1 M.

17. The composition according to claim 1, additionally comprising an amino acid at a concentration of at least 1 mM.

18. The composition according to claim 17, wherein the amino acid is L-histidine.

19. A composition comprising (i) from 50 to 50,000 IU/ml of recombinant Factor VIII, wherein the Factor VIII is a dimer comprising a heavy chain of about 90 to 200 kilodaltons and a light chain of about 80 kilodaltons;

(ii) at least 0.1 mM of a calcium salt;

(iii) at least 1 mM of L-histidine;

(iv) at least 0.1 M of sodium chloride;

(v) at least 0.01 mg/ml of a polyoxyethylene (20) fatty acid ester; and (vi) a zinc salt, optionally in combination with a copper salt, in a concentration of from 0.1 µM to 1 mM.

20. The composition according to claim 1, said composition having a reduced concentration of oxygen and/or containing antioxidants.

21. The composition according to claim 20, wherein the antioxidant is selected from the group consisting of glutathione, acetylcysteine, and methionine.

22. The composition according to claim 1, additionally comprising a mono- or disaccharide in a concentration of at least 100 mg/ml.

23. The composition of claim 1, wherein the heavy chain comprises domains A1 and A2 and the light chain comprises domains A3, C1, and C2.

24. The composition of claim 23, wherein the heavy chain further comprises domain B or a portion thereof.

25. The composition of claim 1, wherein the composition is free of albumin.

26. The composition of claim 1, wherein the composition is free of plasma-derived proteins.

* * * * *